US012171803B2

United States Patent
Overwijk et al.

(10) Patent No.: US 12,171,803 B2
(45) Date of Patent: Dec. 24, 2024

(54) METHODS OF CD40 AND TOLL LIKE RECEPTOR IMMUNE ACTIVATION

(71) Applicants: MEMGEN, INC., Houston, TX (US); BOARD OF REGENTS, THE UNIVERSITY OF TEXAS SYSTEM, Austin, TX (US)

(72) Inventors: Willem Overwijk, Houston, TX (US); Manisha Singh, Houston, TX (US); Patrick Hwu, Houston, TX (US); Mark Cantwell, Meadow Vista, CA (US)

(73) Assignees: MEMGEN, INC., Houston, TX (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 566 days.

(21) Appl. No.: 16/604,818

(22) PCT Filed: Apr. 11, 2018

(86) PCT No.: PCT/US2018/027089
§ 371 (c)(1),
(2) Date: Oct. 11, 2019

(87) PCT Pub. No.: WO2018/191369
PCT Pub. Date: Oct. 18, 2018

(65) Prior Publication Data

US 2020/0353044 A1 Nov. 12, 2020

Related U.S. Application Data

(60) Provisional application No. 62/484,658, filed on Apr. 12, 2017.

(51) Int. Cl.
*A61K 39/00* (2006.01)
*A61K 9/00* (2006.01)
(Continued)

(52) U.S. Cl.
CPC .......... *A61K 38/191* (2013.01); *A61K 9/0019* (2013.01); *A61K 35/76* (2013.01); *A61K 45/06* (2013.01); *A61K 38/177* (2013.01)

(58) Field of Classification Search
None
See application file for complete search history.

(56) References Cited

U.S. PATENT DOCUMENTS 7,495,090 B2 2/2009 Prussak et al.
7,524,944 B2 4/2009 Kipps et al.
(Continued)

FOREIGN PATENT DOCUMENTS

EP 2589654 A1 5/2013
WO WO-03099340 A1 * 12/2003 ....... C07K 14/70575
(Continued)

OTHER PUBLICATIONS

Adams, "Toll-like receptor agonists in cancer therapy," Immunotherapy, 1(6): 949-964 (Year: 2009).*
(Continued)

*Primary Examiner* — M Franco G Salvoza
(74) *Attorney, Agent, or Firm* — Jackson Walker LLP; Leisa Talbert Peschel

(57) ABSTRACT

Provided herein are methods and compositions for treating cancer in an individual comprising administering to the individual an effective amount of a TLR agonist and a chimeric CD154 polypeptide. Also provided herein are methods of enhanced immune function.

10 Claims, 6 Drawing Sheets
Specification includes a Sequence Listing.

Efficacy of combination therapy of ISF35 with different TLR agonists

ISF35 + TLR agonists:

(51) Int. Cl.

| | |
|---|---|
| ***A61K 35/76*** | (2015.01) |
| ***A61K 38/19*** | (2006.01) |
| ***A61K 45/06*** | (2006.01) |
| *A61K 38/17* | (2006.01) |

(56) References Cited

U.S. PATENT DOCUMENTS

| | | | | |
|---|---|---|---|---|
| 7,786,282 | B2 | 8/2010 | Prussak et al. | |
| 7,928,213 | B2 | 4/2011 | Prussak et al. | |
| 8,138,310 | B2 | 3/2012 | Prussak et al. | |
| 2003/0220473 | A1 * | 11/2003 | Prussak | A61P 35/00 435/7.1 |
| 2008/0050340 | A1 * | 2/2008 | Kedl | A61K 47/646 424/85.5 |
| 2008/0318886 | A1 | 12/2008 | Prussak | |
| 2016/0340439 | A1 | 11/2016 | Engleman et al. | |
| 2018/0169241 | A1 | 6/2018 | Cantwell | |
| 2018/0169271 | A1 | 6/2018 | Cantwell et al. | |
| 2020/0165339 | A1 | 5/2020 | Overwijk et al. | |

FOREIGN PATENT DOCUMENTS

| | | | | |
|---|---|---|---|---|
| WO | WO-2007063421 | A2 * | 6/2007 | A61K 39/0011 |
| WO | 2008070743 | A2 | 6/2008 | |
| WO | WO-2016057841 | A1 * | 4/2016 | A61K 39/00 |
| WO | 2017079202 | A1 | 5/2017 | |
| WO | 2017079297 | A1 | 5/2017 | |
| WO | 2018118967 | A1 | 6/2018 | |

OTHER PUBLICATIONS

Diao et al., "Antitumor activity of a novel small molecule TLR7 agonist via immune response induction and tumor microenvironment modulation," Oncology Reports 35: 793-800 (Year: 2016).*

Bonello, S., European Search Report for European Patent Application No. 18784902.1, dated Dec. 15, 2020, 17 pages, European Patent Office.

Beatty, G.L., Li, Y., Long, K.B., "Cancer immunotherapy: activating innate and adaptive immunity through CD40 agonists", Expert Review of Anticancer Therapy, (Dec. 14, 2006), 23 pages, vol. 17, No. 2, Philadelphia, PA.

* cited by examiner

Figure 1. Efficacy of combination therapy of ISF35 with different TLR agonists
ISF35 + TLR agonists:
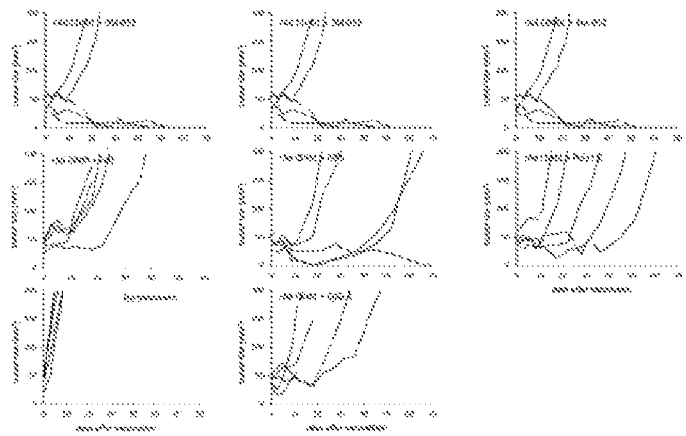

Figure 2. Superior activity of ISF35 versus agonist CD40 antibody combination therapy
rAd.ISF35 vs. anti-CD40 mAb
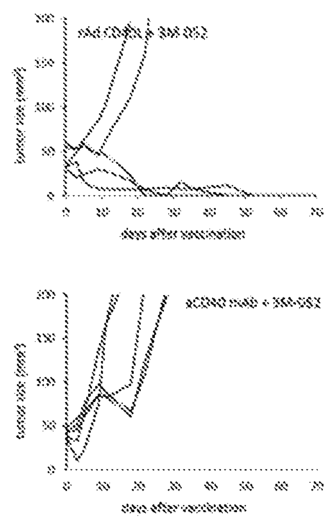

Figure 3. Specificity of ISF35 plus TLR7/8 agonist combination therapy
rAd.ISF35 + 3M-052
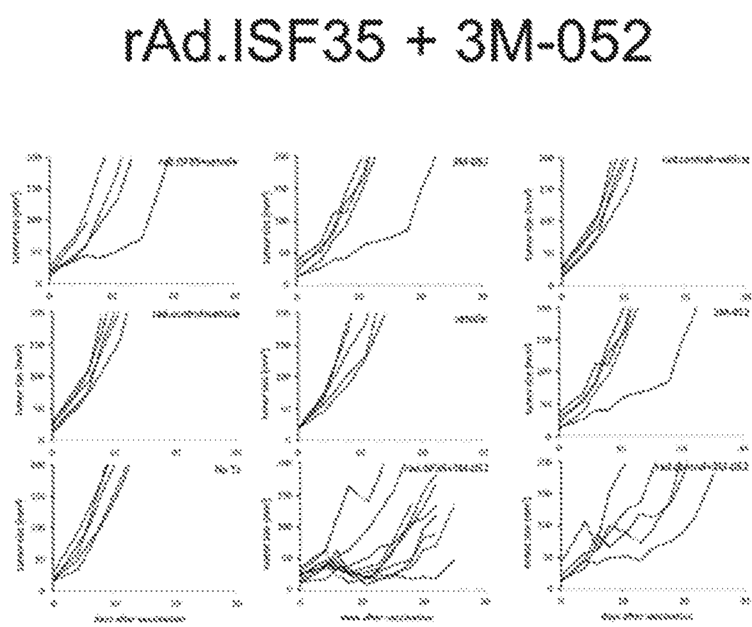

Figure 4. Sequential versus simultaneous treatment schedule
Treatment Schedule
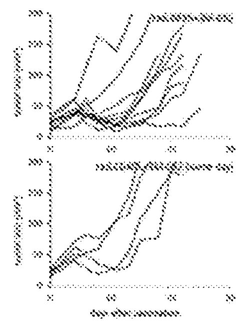
ISF35 on day 0 and 3M-052 1 day later may be slightly better than together on day 0

Figure 5. Dose response activity
ISF35 Dose Response
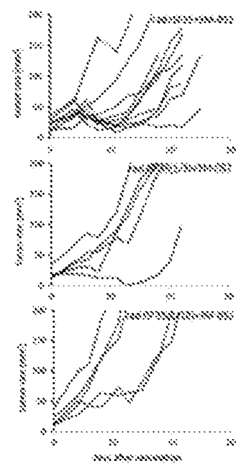
$1 \times 10^{10}$ vp ISF35 better than $3.3 \times 10^{9}$ vp or $1.0 \times 10^{9}$ vp Figure 6. Single versus repeat administration
Single vs. Repeat Dosing
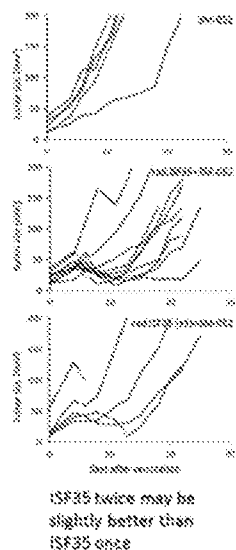

SEQUENCE LISTING

<160> NUMBER OF SEQ ID NOS: 24

<210> SEQ ID NO 1
<211> LENGTH: 783
<212> TYPE: DNA
<213> ORGANISM: Artificial Sequence
<220> FEATURE:
<223> OTHER INFORMATION: ISF30
<220> FEATURE:
<221> NAME/KEY: misc_feature
<222> LOCATION: (1)..(783)

<400> SEQUENCE: 1
atgatagaaa catacagcca accttccccc agatccgtgg caactggact tccagcgagc 60
atgaagattt ttatgtattt acttactgtt ttccttatca cccaaatgat tggatctgtg 120
ctttttgctg tgtatcttca tagaagattg gataaggtcg aagaggaagt aaaccttcat 180
gaagattttg tattcataaa aaagctaaag agatgcaaca aaggagaagg atctttatcc 240
ttgctgaact gtgaggagat gagaaggcaa tttgaagacc ttgtcaagga tataacgtta 300
aacaaagaag agaaaaaaga aaacagcttt gaaatgcaaa gaggtgatga ggatcctcaa 360
attgcagcac acgttgtaag cgaagccaac agtaatgcag catccgttct acagtgggcc 420
aagaaaggat attataccat gaaaagcaac ttggtaaccc tggaaaatgg gaaacagctg 480
acggttaaaa gacaaggact ctattatatc tatgctcaag tcaccttctg ctctaatcgg 540
gagccttcga gtcaacgccc attcatcgtc ggcctctggc tgaagcccag cagtggatct 600
gagagaatct tactcaaggc ggcaaatacc cacagttcct cccagctttg cgagcagcag 660
tctgttcact tgggcggagt gtttgaatta caaccaggtg cttcggtgtt tgtcaatgtg 720
actgatccaa gccaagtgag ccatggcact ggcttcacgt cctttggctt actcaaactc 780
tga 783

<210> SEQ ID NO 2
<211> LENGTH: 759
<212> TYPE: DNA
<213> ORGANISM: Artificial Sequence
<220> FEATURE:
<223> OTHER INFORMATION: ISF31
<220> FEATURE:
<221> NAME/KEY: misc_feature
<222> LOCATION: (1)..(759)

<400> SEQUENCE: 2
atgatcgaaa catacaacca aacttctccc cgatctgcgg ccactggact gcccatcagc 60
atgaaaattt ttatgtattt acttactgtt tttcttatca cccagatgat tgggtcagca 120
ctttttgctg tgtatcttca tagaaggctg gacaagatag aagatgaaag gaatcttcat 180

```
gaagattttg tattcatgaa aacgatacag agatgcaaca caggagaaag atccttatcc    240

ttactgaact gtgaggagat taaaagccag tttgaaggct ttgtgaagga tataatgtta    300

aacaaagagg agacgaagaa agatgaggat cctcaaattg cagcacacgt tgtaagcgaa    360

gccaacagta atgcagcatc cgttctacag tgggccaaga aaggatatta taccatgaaa    420

agcaacttgg taaccctgga aaatgggaaa cagctgacgg ttaaaagaca aggactctat    480

tatatctatg ctcaagtcac cttctgctct aatcgggagc cttcgagtca acgcccattc    540

atcgtcggcc tctggctgaa gcccagcagt ggatctgaga gaatcttact caaggcggca    600

aatacccaca gttcctccca gctttgcgag cagcagtctg ttcacttggg cggagtgttt    660

gaattacaac caggtgcttc ggtgtttgtc aatgtgactg atccaagcca agtgagccat    720

ggcactggct tcacgtcctt tggcttactc aaactctga                           759
```

```
<210> SEQ ID NO 3
<211> LENGTH: 783
<212> TYPE: DNA
<213> ORGANISM: Artificial Sequence
<220> FEATURE:
<223> OTHER INFORMATION: ISF32
<220> FEATURE:
<221> NAME/KEY: misc_feature
<222> LOCATION: (1)..(783)

<400> SEQUENCE: 3

atgatagaaa catacagcca accttccccc agatccgtgg caactggact tccagcgagc     60

atgaagattt ttatgtattt acttactgtt ttccttatca cccaaatgat tggatctgtg    120

ctttttgctg tgtatcttca tagaagattg gataaggtcg aagaggaagt aaaccttcat    180

gaagattttg tattcataaa aaagctaaag agatgcaaca aaggagaagg atctttatcc    240

ttgctgaact gtgaggagat gagaaggcaa tttgaagacc ttgtcaagga tataacgtta    300

aacaaagaag agaaaaaaga aaacagcttt gaaatgcaaa gaggtgatga ggatcctcaa    360

attgcagcac acgttgtaag cgaagccaac agtaatgcag catccgttct acagtgggcc    420

aagaaaggat attataccat gaaaagcaac ttggtaaccc tggaaaatgg gaaacagctg    480

acggttaaaa gacaaggact ctattatatc tatgctcaag tcaccttctg ctctaatcgg    540

gaggcttcga gtcaagcccc attcatcgtc ggcctctggc tgaagcccag cagtggatct    600

gagagaatct tactcaaggc ggcaaatacc cacagttcct cccagctttg cgagcagcag    660

tctgttcact tgggcggagt gtttgaatta caaccaggtg cttcggtgtt tgtcaatgtg    720

actgatccaa gccaagtgag ccatggcact ggcttcacgt cctttggctt actcaaactc    780

tga                                                                  783
```

```
<210> SEQ ID NO 4
<211> LENGTH: 759
<212> TYPE: DNA
<213> ORGANISM: Artificial Sequence
<220> FEATURE:
<223> OTHER INFORMATION: ISF33
<220> FEATURE:
<221> NAME/KEY: misc_feature
<222> LOCATION: (1)..(759)

<400> SEQUENCE: 4

atgatcgaaa catacaacca aacttctccc cgatctgcgg ccactggact gcccatcagc     60

atgaaaattt ttatgtattt acttactgtt tttcttatca cccagatgat tgggtcagca    120
```

```
ctttttgctg tgtatcttca tagaaggctg gacaagatag aagatgaaag gaatcttcat    180

gaagattttg tattcatgaa aacgatacag agatgcaaca caggagaaag atccttatcc    240

ttactgaact gtgaggagat taaaagccag tttgaaggct ttgtgaagga tataatgtta    300

aacaaagagg agacgaagaa agatgaggat cctcaaattg cagcacacgt tgtaagcgaa    360

gccaacagta atgcagcatc cgttctacag tgggccaaga aaggatatta taccatgaaa    420

agcaacttgg taaccctgga aaatgggaaa cagctgacgg ttaaaagaca aggactctat    480

tatatctatg ctcaagtcac cttctgctct aatcgggagg cttcgagtca agccccattc    540

atcgtcggcc tctggctgaa gcccagcagt ggatctgaga gaatcttact caaggcggca    600

aatacccaca gttcctccca gctttgcgag cagcagtctg ttcacttggg cggagtgttt    660

gaattacaac caggtgcttc ggtgtttgtc aatgtgactg atccaagcca agtgagccat    720

ggcactggct tcacgtcctt tggcttactc aaactctga                           759


<210> SEQ ID NO 5
<211> LENGTH: 783
<212> TYPE: DNA
<213> ORGANISM: Artificial Sequence
<220> FEATURE:
<223> OTHER INFORMATION: ISF34
<220> FEATURE:
<221> NAME/KEY: misc_feature
<222> LOCATION: (1)..(783)

<400> SEQUENCE: 5

atgatagaaa catacagcca accttccccc agatccgtgg caactggact tccagcgagc     60

atgaagattt ttatgtattt acttactgtt ttccttatca cccaaatgat tggatctgtg    120

ctttttgctg tgtatcttca tagaagattg gataaggtcg aagaggaagt aaaccttcat    180

gaagattttg tattcataaa aaagctaaag agatgcaaca aaggagaagg atctttatcc    240

ttgctgaact gtgaggagat gagaaggcaa tttgaagacc ttgtcaagga tataacgtta    300

aacaaagaag agaaaaaaga aaacagcttt gaaatgcaaa gaggtgatga ggatcctcaa    360

attgcagcac acgttgtaag cgaagccaac agtaatgcag catccgttct acagtgggcc    420

aagaaaggat attataccat gaaaagcaac ttggtaaccc tggaaaatgg gaaacagctg    480

acggttaaaa gacaaggact ctattatatc tatgctcaag tcaccttctg ctctaatcgg    540

gaggcttcga gtcaagcccc attcatcgtc ggcctctggc tgaagcccag cagtggatct    600

gagagaatct tactcaaggc ggcaaatacc cacagttcct cccagctttg cgagcagcag    660

tctattcact tgggcggagt gtttgaatta caaccaggtg cttcggtgtt tgtcaatgtg    720

actgatccaa gccaagtgag ccatggcact ggcttcacgt cctttggctt actcaaactc    780

tga                                                                  783


<210> SEQ ID NO 6
<211> LENGTH: 759
<212> TYPE: DNA
<213> ORGANISM: Artificial Sequence
<220> FEATURE:
<223> OTHER INFORMATION: ISF35 (MEM40)
<220> FEATURE:
<221> NAME/KEY: misc_feature
<222> LOCATION: (1)..(759)

<400> SEQUENCE: 6

atgatcgaaa catacaacca aacttctccc cgatctgcgg ccactggact gcccatcagc     60

atgaaaattt ttatgtattt acttactgtt tttcttatca cccagatgat tgggtcagca    120
```

```
ctttttgctg tgtatcttca tagaaggctg gacaagatag aagatgaaag gaatcttcat    180

gaagattttg tattcatgaa aacgatacag agatgcaaca caggagaaag atccttatcc    240

ttactgaact gtgaggagat taaaagccag tttgaaggct ttgtgaagga tataatgtta    300

aacaaagagg agacgaagaa agatgaggat cctcaaattg cagcacacgt tgtaagcgaa    360

gccaacagta atgcagcatc cgttctacag tgggccaaga aaggatatta taccatgaaa    420

agcaacttgg taaccctgga aaatgggaaa cagctgacgg ttaaaagaca aggactctat    480

tatatctatg ctcaagtcac cttctgctct aatcgggagg cttcgagtca agccccattc    540

atcgtcggcc tctggctgaa gcccagcagt ggatctgaga gaatcttact caaggcggca    600

aatacccaca gttcctccca gctttgcgag cagcagtcta ttcacttggg cggagtgttt    660

gaattacaac caggtgcttc ggtgtttgtc aatgtgactg atccaagcca agtgagccat    720

ggcactggct tcacgtcctt tggcttactc aaactctga                           759
```

```
<210> SEQ ID NO 7
<211> LENGTH: 783
<212> TYPE: DNA
<213> ORGANISM: Artificial Sequence
<220> FEATURE:
<223> OTHER INFORMATION: ISF36
<220> FEATURE:
<221> NAME/KEY: misc_feature
<222> LOCATION: (1)..(783)

<400> SEQUENCE: 7

atgatagaaa catacagcca accttccccc agatccgtgg caactggact tccagcgagc     60

atgaagattt ttatgtattt acttactgtt ttccttatca cccaaatgat tggatctgtg    120

ctttttgctg tgtatcttca tagaagattg gataaggtcg aagaggaagt aaaccttcat    180

gaagattttg tattcataaa aaagctaaag agatgcaaca aaggagaagg atctttatcc    240

ttgctgaact gtgaggagat gagaaggcaa tttgaagacc ttgtcaagga tataacgtta    300

aacaaagaag agaaaaaaga aaacagcttt gaaatgcaaa gaggtgatga ggatcctcaa    360

attgcagcac acgttgtaag cgaagccaac agtaatgcag catccgttct acagtgggcc    420

aagaaaggat attataccat gaaaagcaac ttggtaaccc tggaaaatgg gaaacagctg    480

acggttaaaa gacaaggact ctattatatc tatgctcaag tcaccttctg ctctaatcgg    540

gaggcttcga gtcaagcccc attcatcgtc ggcctctggc tgaagcccag cagtggatct    600

gagagaatct tactcaaggc ggcaaatacc cacagttccg ccaagccttg cgggcagcag    660

tctattcact tgggcggagt gtttgaatta caaccaggtg cttcgtgttt tgtcaatgtg    720

actgatccaa gccaagtgag ccatggcact ggcttcacgt cctttggctt actcaaactc    780

tga                                                                  783
```

```
<210> SEQ ID NO 8
<211> LENGTH: 759
<212> TYPE: DNA
<213> ORGANISM: Artificial Sequence
<220> FEATURE:
<223> OTHER INFORMATION: ISF37
<220> FEATURE:
<221> NAME/KEY: misc_feature
<222> LOCATION: (1)..(759)

<400> SEQUENCE: 8

atgatcgaaa catacaacca aacttctccc cgatctgcgg ccactggact gcccatcagc     60
```

```
atgaaaattt ttatgtattt acttactgtt tttcttatca cccagatgat tgggtcagca    120

ctttttgctg tgtatcttca tagaaggctg gacaagatag aagatgaaag gaatcttcat    180

gaagattttg tattcatgaa aacgatacag agatgcaaca caggagaaag atccttatcc    240

ttactgaact gtgaggagat taaaagccag tttgaaggct ttgtgaagga tataatgtta    300

aacaaagagg agacgaagaa agatgaggat cctcaaattg cagcacacgt tgtaagcgaa    360

gccaacagta atgcagcatc cgttctacag tgggccaaga aaggatatta taccatgaaa    420

agcaacttgg taaccctgga aaatgggaaa cagctgacgg ttaaaagaca aggactctat    480

tatatctatg ctcaagtcac cttctgctct aatcgggagg cttcgagtca agccccattc    540

atcgtcggcc tctggctgaa gcccagcagt ggatctgaga gaatcttact caaggcggca    600

aatacccaca gttccgccaa gccttgcggg cagcagtcta ttcacttggg cggagtgttt    660

gaattacaac caggtgcttc ggtgtttgtc aatgtgactg atccaagcca agtgagccat    720

ggcactggct tcacgtcctt tggcttactc aaactctga                           759
```

```
<210> SEQ ID NO 9
<211> LENGTH: 783
<212> TYPE: DNA
<213> ORGANISM: Artificial Sequence
<220> FEATURE:
<223> OTHER INFORMATION: ISF38
<220> FEATURE:
<221> NAME/KEY: misc_feature
<222> LOCATION: (1)..(783)

<400> SEQUENCE: 9

atgatagaaa catacagcca accttccccc agatccgtgg caactggact tccagcgagc     60

atgaagattt ttatgtattt acttactgtt ttccttatca cccaaatgat tggatctgtg    120

ctttttgctg tgtatcttca tagaagattg gataaggtcg aagaggaagt aaaccttcat    180

gaagattttg tattcataaa aaagctaaag agatgcaaca aaggagaagg atctttatcc    240

ttgctgaact gtgaggagat gagaaggcaa tttgaagacc ttgtcaagga tataacgtta    300

aacaaagaag agaaaaaaga aaacagcttt gaaatgcaaa gaggtgatga ggatcctcaa    360

attgcagcac acgttgtaag cgaagccaac agtaatgcag catccgttct acagtgggcc    420

aagaaaggat attataccat gaaaagcaac ttggtaaccc tggaaaatgg gaaacagctg    480

acggttaaaa gacaaggact ctattatatc tatgctcaag tcaccttctg ctctaatcgg    540

gagccttcga gtcaacgccc attcatcgtc ggcctctggc tgaagcccag cagtggatct    600

gagagaatct tactcaaggc ggcaaatacc cacagttcct cccagctttg cgagcagcag    660

tctattcact tgggcggagt gtttgaatta caaccaggtg cttcggtgtt tgtcaatgtg    720

actgatccaa gccaagtgag ccatggcact ggcttcacgt cctttggctt actcaaactc    780

tga                                                                  783
```

```
<210> SEQ ID NO 10
<211> LENGTH: 759
<212> TYPE: DNA
<213> ORGANISM: Artificial Sequence
<220> FEATURE:
<223> OTHER INFORMATION: ISF39
<220> FEATURE:
<221> NAME/KEY: misc_feature
<222> LOCATION: (1)..(759)

<400> SEQUENCE: 10

atgatcgaaa catacaacca aacttctccc cgatctgcgg ccactggact gcccatcagc     60
```

```
atgaaaattt ttatgtattt acttactgtt tttcttatca cccagatgat tgggtcagca    120

ctttttgctg tgtatcttca tagaaggctg gacaagatag aagatgaaag gaatcttcat    180

gaagattttg tattcatgaa aacgatacag agatgcaaca caggagaaag atccttatcc    240

ttactgaact gtgaggagat taaaagccag tttgaaggct ttgtgaagga tataatgtta    300

aacaaagagg agacgaagaa agatgaggat cctcaaattg cagcacacgt tgtaagcgaa    360

gccaacagta atgcagcatc cgttctacag tgggccaaga aaggatatta taccatgaaa    420

agcaacttgg taaccctgga aaatgggaaa cagctgacgg ttaaaagaca aggactctat    480

tatatctatg ctcaagtcac cttctgctct aatcgggagc cttcgagtca acgcccattc    540

atcgtcggcc tctggctgaa gcccagcagt ggatctgaga gaatcttact caaggcggca    600

aatacccaca gttcctccca gctttgcgag cagcagtcta ttcacttggg cggagtgttt    660

gaattacaac caggtgcttc ggtgtttgtc aatgtgactg atccaagcca agtgagccat    720

ggcactggct tcacgtcctt tggcttactc aaactctga                           759
```

```
<210> SEQ ID NO 11
<211> LENGTH: 783
<212> TYPE: DNA
<213> ORGANISM: Artificial Sequence
<220> FEATURE:
<223> OTHER INFORMATION: ISF40
<220> FEATURE:
<221> NAME/KEY: misc_feature
<222> LOCATION: (1)..(783)

<400> SEQUENCE: 11

atgatagaaa catacagcca accttccccc agatccgtgg caactggact tccagcgagc     60

atgaagattt ttatgtattt acttactgtt ttccttatca cccaaatgat tggatctgtg    120

ctttttgctg tgtatcttca tagaagattg gataaggtcg aagaggaagt aaaccttcat    180

gaagattttg tattcataaa aaagctaaag agatgcaaca aaggagaagg atctttatcc    240

ttgctgaact gtgaggagat gagaaggcaa tttgaagacc ttgtcaagga tataacgtta    300

aacaaagaag agaaaaaaga aaacagcttt gaaatgcaaa gaggtgatga ggatcctcaa    360

attgcagcac acgttgtaag cgaagccaac agtaatgcag catccgttct acagtgggcc    420

aagaaaggat attataccat gaaaagcaac ttggtaaccc tggaaaatgg gaaacagctg    480

acggttaaaa gacaaggact ctattatatc tatgctcaag tcaccttctg ctctaatcgg    540

gagccttcga gtcaacgccc attcatcgtc ggcctctggc tgaagcccag cagtggatct    600

gagagaatct tactcaaggc ggcaaatacc cacagttccg ccaagccttg cgggcagcag    660

tctattcact tgggcggagt gtttgaatta caaccaggtg cttcggtgtt tgtcaatgtg    720

actgatccaa gccaagtgag ccatggcact ggcttcacgt cctttggctt actcaaactc    780

tga                                                                  783
```

```
<210> SEQ ID NO 12
<211> LENGTH: 759
<212> TYPE: DNA
<213> ORGANISM: Artificial Sequence
<220> FEATURE:
<223> OTHER INFORMATION: ISF41
<220> FEATURE:
<221> NAME/KEY: misc_feature
<222> LOCATION: (1)..(759)

<400> SEQUENCE: 12
```

```
atgatcgaaa catacaacca aacttctccc cgatctgcgg ccactggact gcccatcagc     60

atgaaaattt ttatgtattt acttactgtt tttcttatca cccagatgat tgggtcagca    120

ctttttgctg tgtatcttca tagaaggctg gacaagatag aagatgaaag gaatcttcat    180

gaagattttg tattcatgaa aacgatacag agatgcaaca caggagaaag atccttatcc    240

ttactgaact gtgaggagat taaaagccag tttgaaggct ttgtgaagga tataatgtta    300

aacaaagagg agacgaagaa agatgaggat cctcaaattg cagcacacgt tgtaagcgaa    360

gccaacagta atgcagcatc cgttctacag tgggccaaga aaggatatta taccatgaaa    420

agcaacttgg taaccctgga aaatgggaaa cagctgacgg ttaaaagaca aggactctat    480

tatatctatg ctcaagtcac cttctgctct aatcgggagc cttcgagtca acgcccattc    540

atcgtcggcc tctggctgaa gcccagcagt ggatctgaga gaatcttact caaggcggca    600

aatacccaca gttccgccaa gccttgcggg cagcagtcta ttcacttggg cggagtgttt    660

gaattacaac caggtgcttc ggtgtttgtc aatgtgactg atccaagcca agtgagccat    720

ggcactggct tcacgtcctt tggcttactc aaactctga                           759
```

```
<210> SEQ ID NO 13
<211> LENGTH: 260
<212> TYPE: PRT
<213> ORGANISM: Artificial Sequence
<220> FEATURE:
<223> OTHER INFORMATION: Chimeric human/mouse CD40 ligand
<220> FEATURE:
<221> NAME/KEY: PEPTIDE
<222> LOCATION: (1)..(260)

<400> SEQUENCE: 13

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
```

```
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 14
<211> LENGTH: 252
<212> TYPE: PRT
<213> ORGANISM: Artificial Sequence
<220> FEATURE:
<223> OTHER INFORMATION: ISF31
<220> FEATURE:
<221> NAME/KEY: PEPTIDE
<222> LOCATION: (1)..(252)

<400> SEQUENCE: 14

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Pro Ser Ser
                165                 170                 175

Gln Arg Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Val His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 15
<211> LENGTH: 260
<212> TYPE: PRT
<213> ORGANISM: Artificial Sequence
<220> FEATURE:
<223> OTHER INFORMATION: ISF32
```

<220> FEATURE:
<221> NAME/KEY: PEPTIDE
<222> LOCATION: (1)..(260)

<400> SEQUENCE: 15

```
Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260
```

<210> SEQ ID NO 16
<211> LENGTH: 252
<212> TYPE: PRT
<213> ORGANISM: Artificial Sequence
<220> FEATURE:
<223> OTHER INFORMATION: ISF33
<220> FEATURE:
<221> NAME/KEY: PEPTIDE
<222> LOCATION: (1)..(252)

<400> SEQUENCE: 16

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45
```

```
Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Val His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 17
<211> LENGTH: 260
<212> TYPE: PRT
<213> ORGANISM: Artificial Sequence
<220> FEATURE:
<223> OTHER INFORMATION: Artificial Sequence
<220> FEATURE:
<221> NAME/KEY: PEPTIDE
<222> LOCATION: (1)..(260)

<400> SEQUENCE: 17

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140
```

```
Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Ile His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 18
<211> LENGTH: 252
<212> TYPE: PRT
<213> ORGANISM: Artificial Sequence
<220> FEATURE:
<223> OTHER INFORMATION: ISF35
<220> FEATURE:
<221> NAME/KEY: PEPTIDE
<222> LOCATION: (1)..(252)

<400> SEQUENCE: 18

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Ile His Leu Gly Gly Val Phe Glu Leu Gln Pro
    210                 215                 220
```

```
Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 19
<211> LENGTH: 260
<212> TYPE: PRT
<213> ORGANISM: Artificial Sequence
<220> FEATURE:
<223> OTHER INFORMATION: ISF36
<220> FEATURE:
<221> NAME/KEY: PEPTIDE
<222> LOCATION: (1)..(260)

<400> SEQUENCE: 19

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ala Lys Pro Cys Gly Gln Gln Ser Ile His Leu
    210                 215                 220

Gly Gly Val Phe Glu Leu Gln Pro Gly Ala Ser Cys Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 20
<211> LENGTH: 252
<212> TYPE: PRT
<213> ORGANISM: Artificial Sequence
<220> FEATURE:
<223> OTHER INFORMATION: ISF37
<220> FEATURE:
<221> NAME/KEY: PEPTIDE
```

```
<222> LOCATION: (1)..(252)

<400> SEQUENCE: 20

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ala Lys Pro
        195                 200                 205

Cys Gly Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 21
<211> LENGTH: 260
<212> TYPE: PRT
<213> ORGANISM: Artificial Sequence
<220> FEATURE:
<223> OTHER INFORMATION: ISF38
<220> FEATURE:
<221> NAME/KEY: PEPTIDE
<222> LOCATION: (1)..(260)

<400> SEQUENCE: 21

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80
```

```
Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Ile His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 22
<211> LENGTH: 252
<212> TYPE: PRT
<213> ORGANISM: Artificial Sequence
<220> FEATURE:
<223> OTHER INFORMATION: ISF39
<220> FEATURE:
<221> NAME/KEY: PEPTIDE
<222> LOCATION: (1)..(252)

<400> SEQUENCE: 22

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160
```

```
Tyr Ile Tyr Ala Gln Val Thr Phe Cys Ser Asn Arg Glu Pro Ser Ser
                165                 170                 175

Gln Arg Pro Phe Ile Val Gly Leu Trp Leu Lys Pro Ser Ser Gly Ser
            180                 185                 190

Glu Arg Ile Leu Leu Lys Ala Ala Asn Thr His Ser Ser Gln Leu
        195                 200                 205

Cys Glu Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 23
<211> LENGTH: 260
<212> TYPE: PRT
<213> ORGANISM: Artificial Sequence
<220> FEATURE:
<223> OTHER INFORMATION: ISF40
<220> FEATURE:
<221> NAME/KEY: PEPTIDE
<222> LOCATION: (1)..(260)

<400> SEQUENCE: 23

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ala Lys Pro Cys Gly Gln Gln Ser Ile His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255
```

Leu Leu Lys Leu
260

<210> SEQ ID NO 24
<211> LENGTH: 252
<212> TYPE: PRT
<213> ORGANISM: Artificial Sequence
<220> FEATURE:
<223> OTHER INFORMATION: ISF41
<220> FEATURE:
<221> NAME/KEY: PEPTIDE
<222> LOCATION: (1)..(252)

<400> SEQUENCE: 24

Met Ile Glu Thr Tyr Asn Gln Thr Ser Pro Arg Ser Ala Ala Thr Gly
1 5 10 15

Leu Pro Ile Ser Met Lys Ile Phe Met Tyr Leu Leu Thr Val Phe Leu
20 25 30

Ile Thr Gln Met Ile Gly Ser Ala Leu Phe Ala Val Tyr Leu His Arg
35 40 45

Arg Leu Asp Lys Ile Glu Asp Glu Arg Asn Leu His Glu Asp Phe Val
50 55 60

Phe Met Lys Thr Ile Gln Arg Cys Asn Thr Gly Glu Arg Ser Leu Ser
65 70 75 80

Leu Leu Asn Cys Glu Glu Ile Lys Ser Gln Phe Glu Gly Phe Val Lys
85 90 95

Asp Ile Met Leu Asn Lys Glu Glu Thr Lys Lys Asp Glu Asp Pro Gln
100 105 110

Ile Ala Ala His Val Val Ser Glu Ala Asn Ser Asn Ala Ala Ser Val
115 120 125

Leu Gln Trp Ala Lys Lys Gly Tyr Tyr Thr Met Lys Ser Asn Leu Val
130 135 140

Thr Leu Glu Asn Gly Lys Gln Leu Thr Val Lys Arg Gln Gly Leu Tyr
145 150 155 160

Tyr Ile Tyr Ala Gln Val Thr Phe Cys Ser Asn Arg Glu Pro Ser Ser
165 170 175

Gln Arg Pro Phe Ile Val Gly Leu Trp Leu Lys Pro Ser Ser Gly Ser
180 185 190

Glu Arg Ile Leu Leu Lys Ala Ala Asn Thr His Ser Ser Ala Lys Pro
195 200 205

Cys Gly Gln Gln Ser Ile His Leu Gly Gly Val Phe Glu Leu Gln Pro
210 215 220

Gly Ala Ser Val Phe Val Asn Val Thr Asp Pro Ser Gln Val Ser His
225 230 235 240

Gly Thr Gly Phe Thr Ser Phe Gly Leu Leu Lys Leu
245 250

METHODS OF CD40 AND TOLL LIKE RECEPTOR IMMUNE ACTIVATION

PARTIES TO JOINT RESEARCH AGREEMENT

The present invention was made as a result of activities undertaken within the scope of a joint research agreement that was in effect at the time the present invention was made. The parties to said joint research agreement are The University of Texas M.D. Anderson Cancer Center, a member institution of The University of Texas System, and Memgen, LLC.

BACKGROUND OF THE INVENTION

1. Field of the Invention

The present invention relates generally to the field of immunology and medicine. More particularly, it concerns compositions and methods of enhancing immune function.

2. Description of Related Art

Although the immunogenic nature of melanoma makes the disease highly susceptible to immunotherapy, metastatic melanoma remains highly resistant to established immunotherapies. In addition, brain metastasis is a major clinical problem in patients with advanced melanoma, and the incidence of brain metastasis is increasing every year. Cancer vaccines have increased the number and activity of T cells that recognize tumor-associated antigens in many cases, however, there is a lack of robust clinical response with this treatment method.

Cytotoxic CD8 T cells suppress melanoma growth and are associated with overall patient survival; however, therapies that induce tumor-specific CD8 T cells have had limited clinical success. For example, CD40 agonist antibodies induce tumor-specific CD8 T cells in mice as well as in patients with melanoma, but most patients do not respond to this therapy. While agonistic CD40 antibodies have been shown to generate strong tumor specific CD8 T cell response, systemic anti-CD40 therapy has been associated with cytokine release syndrome and liver toxicity. Thus, there is a need for immunotherapy that produces a strong CD8 T cell response in tumors with a robust therapeutic effect, and simultaneously being safe and well tolerated.

SUMMARY OF THE INVENTION

Several of the present embodiments provide methods and compositions for enhancing immune function by the combination of Toll Like Receptor (TLR) agonist and a chimeric CD154 polypeptide. In one embodiment, there is provided a method of enhancing immune function comprising administering to a subject at least one TLR agonist and a chimeric CD154 polypeptide comprising (a) an extracellular subdomain of human CD154 that binds to a human CD154 receptor and (b) an extracellular subdomain of non-human CD154 that replaces a cleavage site of human CD154. Alternatively, the CD154 polypeptide may comprise (a) an extracellular subdomain of human CD154 that binds to a human CD154 receptor and (b) any peptide segment that replaces a cleavage site of human CD 154 but otherwise maintains the binding function of the CD154 polypeptide. More particularly, the peptide should generally maintain an overall secondary and tertiary structure of the CD154 polypeptide that maintains its binding specificity, which may include maintaining the spacing of CD 154 sequences flanking the peptide once inserted.

In certain aspects, the at least one TLR agonist is a TLR1, TLR2, TLR3, TLR4, TLR5, TLR6, TLR7, TLR8, TLR9, TLR10, TLR11, or TLR7/8 agonist.

In certain aspects, the extracellular subdomain of non-human CD154 is an extracellular subdomain of murine CD154. For example, the chimeric CD154 polypeptide is selected from the group consisting of ISF30, ISF31, ISF32, ISF33, ISF34, ISF35, ISF36, ISF37, ISF38, ISF39, ISF40, and ISF41. In particular, the chimeric CD154 polypeptide is ISF35.

In further aspects, the chimeric CD154 polypeptide is administered to a subject by (i) providing a coding region for the chimeric CD154 polypeptide in an expression vector and under control of a promoter active in a eukaryotic cell, and (ii) culturing said immune cell and said eukaryotic cell under conditions supporting expression of said chimeric CD154 polypeptide. In some aspects, the expression cassette is in a viral vector. For example, the viral vector is an adenoviral vector, a retroviral vector, a pox viral vector, a herpes viral vector, an adeno-associated viral vector, or a polyoma viral vector. In particular, the viral vector is an adenoviral vector.

In additional embodiments, methods of treating a cancer in a subject are provided comprising administering to the subject an effective amount of at least one TLR agonist and a chimeric CD154 polypeptide comprising (a) an extracellular subdomain of human CD154 that binds to a human CD154 receptor and (b) an extracellular subdomain of non-human CD154 that replaces a cleavage site of human CD154. In particular, the subject is a human subject. Alternatively, the CD154 polypeptide may comprise (a) an extracellular subdomain of human CD154 that binds to a human CD154 receptor and (b) any peptide segment that replaces a cleavage site of human CD 154 but otherwise maintains the binding function of the CD154 polypeptide. More particularly, the peptide should generally maintain the overall secondary and tertiary structure of the CD154 polypeptide, which may include maintaining the spacing of CD 154 sequences flanking the peptide once inserted.

In some aspects, the chimeric CD154 polypeptide is administered before the at least one TLR agonist, simultaneous with the at least one TLR agonist, or after the at least one TLR agonist.

In some aspects, the chimeric CD154 polypeptide and/or the TLR agonist are administered intravenously, intraperitoneally, intratracheally, intratumorally, intramuscularly, endoscopically, intralesionally, percutaneously, subcutaneously, regionally, or by direct injection or perfusion. In certain aspects, the chimeric CD154 polypeptide and/or the at least one immune checkpoint inhibitor are administered locally or regionally.

In further aspects, the cancer is bladder cancer, breast cancer, clear cell kidney cancer, head/neck squamous cell carcinoma, lung squamous cell carcinoma, melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL). In particular, the cancer is melanoma. Even more particularly, the melanoma is metastatic melanoma.

In further aspects, the combination therapy further comprises at least one additional therapeutic agent. For example, the at least one additional therapeutic agent is chemotherapy, immunotherapy, surgery, radiotherapy, or biotherapy.

In some aspects, the chimeric CD154 polypeptide is provided by administering to said subject a coding region for the chimeric CD154 polypeptide in an expression vector and under control of a promoter active in a eukaryotic cell. In certain aspects, the expression cassette is in a viral vector. For example, the viral vector is an adenoviral vector. In other aspects, the chimeric CD154 polypeptide is administered to said subject.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Efficacy of combination therapy of ISF35 with different TLR agonists. Tumor growth curves of B16.F10 tumors subcutaneously implanted in C54/BL6 mice. Individual animal tumor growth curves are shown.

FIG. 2: Superior activity of ISF35 versus agonist CD40 antibody combination therapy. Tumor growth curves of B16.F10 tumors subcutaneously implanted in C54/BL6 mice. Individual animal tumor growth curves are shown.

FIG. 3. Specificity of ISF35 plus TLR agonist combination therapy. Tumor growth curves of B16.F10 tumors subcutaneously implanted in C54/BL6 mice. Individual animal tumor growth curves are shown.

FIG. 4. Sequential versus simultaneous treatment schedule. Tumor growth curves of B16.F10 tumors subcutaneously implanted in C54/BL6 mice. Individual animal tumor growth curves are shown. Drugs were intratumorally injected either simultaneously on Day 0 or sequentially on Day 0 and Day 1.

FIG. 5. Dose response activity. Tumor growth curves of B16.F10 tumors subcutaneously implanted in C54/BL6 mice. Individual animal tumor growth curves are shown. ISFS35 was intratumorally injected at increasing dose levels.

FIG. 6. Single versus repeat dosing. Tumor growth curves of B16.F10 tumors subcutaneously implanted in C54/BL6 mice. Individual animal tumor growth curves are shown.

DESCRIPTION OF ILLUSTRATIVE EMBODIMENTS

The present disclosure overcomes several major problems associated with current technologies by providing methods and compositions for enhancing function of an immune cell by providing a combination of at least one TLR agonist and a chimeric CD154 polypeptide.

The present disclosure further provides a method of treating a cancer in a subject by providing to the subject an effective amount of at least one TLR agonist and a chimeric CD154 polypeptide. In certain embodiments, the cancer is metastatic melanoma.

Particularly, the chimeric CD154 polypeptide in the methods of the present disclosure comprises an extracellular subdomain of human CD154 that binds to a human CD154 receptor and a non-human CD154 cleavage site. For example, an extracellular subdomain of human CD154 which comprises a cleavage site is replaced by an extracellular subdomain of non-human CD154, such as murine CD154. In particular embodiments, the chimeric CD154 polypeptide is ISF35. In one method, the chimeric CD154 polypeptide is delivered in an expression cassette, such as an adenoviral vector, encoding the polypeptide, in particular under the control of a promoter active in a eukaryotic cell.

In some aspects, the TLR agonist is a TLR1, TLR2, TLR3, TLR4, TLR5, TLR6, TLR7, TLR8, TLR9, TLR10, TLR11, or TLR7/8 agonist.

Thus, the methods provided herein allow for the treatment of a cancer and/or immune function enhancement which can that produce a robust therapeutic effect. Further embodiments and advantages of the present disclosure are described below.

II. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, in particular below 0.01%. Most particular is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "chimeric" is defined as having sequences from at least two different species. For example, a chimeric CD154 polypeptide is chimeric in that it is comprised of CD154 domains or subdomains from at least two different species, for example human and mouse CD154.

As used herein, the term "chimeric CD154" or "chimeric ISF construct" refers to a ligand comprised of at least one domain or subdomain of CD154 from one species and at least one domain or subdomain of CD154 from a different species. In certain embodiments, the at least two species from which the chimeric CD154 is derived are human and murine CD154.

As used herein, the term "subdomain" refers to a sequence of at least two amino acids that is part of a domain of CD154. A "subdomain" also encompasses an amino acid sequence from which one or more amino acids have been deleted, added, or has been modified, including one or more amino acids truncated from an end of the sequence.

As used herein, the term "cleavage site" refers to a sequence of amino acids that is recognized by proteases, typically matrix metalloproteases (MMP) that cleave CD154 from the surface of the expressing cell. The cleavage site of CD154 is typically found at or around the boundaries of domains III and IV of CD154. For example, one such cleavage site comprises the region approximately between amino acids 108 and 116 of human CD154.

As used herein, the term "corresponding" refers to the sequence of nucleotides or amino acids of CD154 of one species that is homologous to a nucleotide or amino acid sequence of CD154 of another species. This homology is based on the similarity in secondary structure, such as the location of domain boundaries, among CD154 of different species.

As used herein, the phrases "less susceptible to cleavage" or "reduced cleavage" refer to the higher resistance of a chimeric CD154 to proteolytic cleavage compared to that of native human CD154, as measured by the amount of soluble CD154 generated by a given number of cells over a period of time. In particular, a chimeric CD154 of the present invention is "less susceptible to cleavage" because it is cleaved at a rate at least 50%, at least 75%, or at least 90% less than that of native CD154.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid and/or a site at or near where DNA synthesis initiates. As an example, an ori for EBV includes FR sequences (20 imperfect copies of a 30 bp repeat), and particularly DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present invention may also use genetically engineered replication origin of EBV, such as by insertion or mutation of individual elements, as specifically described in Lindner, et. al., 2008.

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control" and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" or co-expressed" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" or "co-expressed" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is in particular chimeric, i.e., composed of heterologous molecules.

"Homology" refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are "substantially homologous" to each other when at least about 80%, in particular at least about 90%, and most particularly at least about 95% of the nucleotides, or amino acids, respectively match over a defined length of the molecules, as determined using the methods above.

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

The term "therapeutic benefit" used throughout this application refers to anything that promotes or enhances the well-being of the patient with respect to the medical treatment of his cancer. A list of non-exhaustive examples of this includes extension of the patient's life by any period of time; decrease or delay in the neoplastic development of the disease; decrease in hyperproliferation; reduction in tumor growth; delay of metastases; reduction in the proliferation rate of a cancer cell or tumor cell; induction of apoptosis in any treated cell or in any cell affected by a treated cell; and a decrease in pain to the patient that can be attributed to the patient's condition.

An "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of individuals.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multi-specific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The term "TLR agonist" refers to a molecule that that stimulates a TLR receptor.

As used herein, the terms "CD40 ligand", "CD40-L" and "CD154" are used interchangeably herein. For example, an adenoviral construct encoding a chimeric CD40 ligand may be referred to as ad-CD40L.

III. CD40 and CD40 Ligand

CD40 is 50 Kd glycoprotein expressed on the surface of B cells, dendritic cells, normal epithelium and some epithelial carcinomas (Briscoe et al, 1998). The ligand for CD40, CD40L, is expressed on activated T lymphocytes, human dendritic cells, human vascular endothelial cells, smooth muscle cells, and macrophages. CD40L exists on such cells as a trimeric structure, which induces oligomerization of its receptor upon binding.

CD40 ligand (CD40-L or gp39) is a type II membrane polypeptide having an extracellular region at its C-terminus, a transmembrane region and an intracellular region at its N-terminus. The CD40 ligand has been cloned and sequenced, and nucleic acid and amino acid sequences have been reported from human (GenBank accession numbers Z15017/S49392, D31793-7, X96710, L07414 and X67878/S50586), murine (GenBank accession number X65453), bovine (GenBank accession number Z48469), canine (GenBank accession number AF086711), feline (GenBank accession number AF079105) and rat (GenBank Accession Numbers AF116582, AF013985). Such murine, bovine, canine, feline and rat sequences are also disclosed in U.S. Pat. No. 6,482,411, incorporated herein by reference. Additional CD40 ligand nucleic acid and amino acid sequences are disclosed in U.S. Pat. Nos. 5,565,321 and 5,540,926, incorporated herein by reference, and mutant CD40 ligand sequences are disclosed in U.S. Pat. No. 5,716,805 and U.S. patent application Ser. Nos. 08/484,624 and 09/088,913, each of which is incorporated herein by reference.

In some embodiments, one or more CD40 agonists, such as CD40 ligands and/or agonistic anti-CD40 antibodies, may be used in combination with one or more immune checkpoint inhibitors to enhance immune function or to treat a neoplastic condition. For example, CD40 ligand polypeptides known in the art can be used in a combination therapy to treat cancer (U.S. Pat. No. 6,482,411, incorporated herein by reference). All CD40 agonists are suitable for use in the methods provided herein, so long as they bind to and activate one or more CD40 receptors on a neoplastic cell. A CD40 agonist that binds to and activates a CD40 receptor on a neoplastic cell is a biological or chemical component or agent that stimulates cell signaling via CD40 in such cells. For example, the CD40 agonist is an agonistic anti-CD40 antibody, or antigen-binding fragment thereof, including, but not limited to, at least a first scFv, Fv, Fab', Fab or $F(ab')_2$ antigen-binding region of an anti-CD40 antibody. In certain aspects, the CD40 agonist is a human, humanized or part-human chimeric anti-CD40 antibody or antigen-binding fragment thereof. In other aspects, the CD40 agonist is an anti-CD40 monoclonal antibody, including, but not limited to, the G28-5, mAb89, EA-5 or S2C6 monoclonal antibody, or an antigen-binding fragment thereof.

A. Chimeric CD154 Polypeptides

CD154 (also known as CD40 ligand) is one member of a larger family of ligands, collectively referred to as the TNF superfamily (Gruss et al, Cytokines Mol Ther, 1:75-105, 1995 and Locksley et al, Cell, 104:487-501, 2001). Members of the TNF superfamily include Fas ligand ("FasL"), TNFα, LTα, lymphotoxin (TNFβ), CD154, TRAIL, CD70, CD30 ligand, 4-1BB ligand, APRIL, TWEAK, RANK ligand, LIGHT, AITR ligand, ectodysplasin, BLYS, VEGI, and OX40 ligand. TNF superfamily members share a conserved secondary structure comprising four domains: domain I, the intracellular domain; domain II, which spans the cell membrane and is known as the transmembrane domain; domain III, which consists of the extracellular amino acids closest to the cell membrane; and domain IV, the distal extracellular domain. Typically, at least a part of domain IV can be cleaved from the parent molecule. The cleaved fragment often exhibits the same biological activity of the intact ligand and is conventionally referred to as a "soluble form" of the TNF family member. Soluble versions of CD40 ligand can be made from the extracellular region, or a fragment thereof, and a soluble CD40 ligand has been found in culture supernatants from cells that express a membrane-bound version of CD40 ligand, such as EL-4 cells.

The interactions between CD154 and its cognate receptor, CD40, are critical for immune recognition. (Banchereau J. et al., *Annu. Rev. Immunol.* 12:881-922, 1994). CD154 is transiently expressed on $CD4^+$ T cells following T cell receptor engagement by antigen presenting cells through MHC class II molecules (Cantwell M. et al., *Nat. Med.,* 3:984-989, 1997). This, in turn, can cause activation of CD40-expressing antigen presenting cells (APCs), including B cells, dendritic cells, monocytes, and macrophages (Ranheim E. A. et al., *Cell. Immunol.,* 161:226-235, 1995). Such CD40 activated cells can set off a cascade of immune-activating events that lead to a specific and effective immune response against foreign antigens, such as viruses or tumors.

It is known in the art that at least part of human CD154 is cleaved from the parent molecule and becomes a soluble molecule, however, the soluble form is generally undesirable. Thus, the chimeric CD154 polypeptide of the present disclosure can be formed by exchanging an amino acid, or an amino acid sequence, of human CD154 that comprises a cleavage site recognized by proteolytic enzymes with an amino acid, or amino acid sequence, of non-human CD154, that does not contain this cleavage site. In certain embodiments, the non-human CD154 is murine CD154. Alternatively, the chimeric CD154 polypeptide can include a point mutation at the cleavage site.

In some embodiments, the chimeric CD154 polynucleotide sequence comprises a first nucleotide sequence encoding an extracellular subdomain of non-human CD154 that corresponds to and replaces a cleavage site of human CD154. The chimeric CD154 polypeptide can be produced by replacing a subdomain of human CD154 containing a CD154 cleavage site with the corresponding subdomain of non-human CD154 results in a chimeric CD154 that is markedly less susceptible to cleavage than human CD154. In other embodiments, the amino acids of the cleavage site are modified, altered or deleted to decrease susceptibility to cleavage by a protease. The first nucleotide sequence can be operatively linked to a second nucleotide sequence that encodes an extracellular subdomain of human CD154 involved in binding to a human CD154 receptor, such as the CD40 ligand. In this way, the polynucleotide sequence of the present disclosure encodes a chimeric CD154 that binds to human cells expressing the CD154 receptor. Moreover, in some aspects, an extracellular domain of murine and human CD154 includes at least one amino acid, or a sequence of amino acids, that allows expression of the molecule on the membranes of murine and human cells.

The chimeric CD154 polypeptides of the present disclosure may be chimeric in that they can be comprised of CD154 domains or subdomains from at least two different species, in some cases human and mouse CD154. These polypeptides are designated “immune stimulatory factors”, or ISF’s, because they combine human and non-human CD154 regions to maximize stimulation of the immune response. Specifically, at least one domain or subdomain of CD154 that contains a cleavage site of human CD154 is replaced with a corresponding domain or subdomain of non-human CD154, in particular murine CD154. In addition, the chimeric polypeptide is composed of a domain or subdomain of human CD154 that is responsible for binding a CD154 receptor.

Chimeric CD154 or CD40L polypeptides for use in the present disclosure are described in U.S. Pat. Nos. 7,495,090 and 7,928,213, both incorporated herein by reference. For example, domain IV of human CD154 can be linked to domains I, II and III of murine CD154. Examples of such in particular polynucleotide sequences are provided herein as SEQ ID. NOS. 1, 3, 5, 7, 9 and 11 and encode chimeric CD154 constructs designated as ISF 30, 32, 34, 36, 38 and 40, respectively. Additionally, domain IV of human CD154 may be linked to domains I, II and III of human CD154. Examples of such polynucleotide sequences are provided as SEQ ID. NOS. 2, 4, 6, 8, 10 and 12, and encode chimeric CD154 constructs are designated ISF 31, 33, 35, 37, 39 and 41, respectively. In particular, the chimeric CD154 polypeptide is ISF35.

B. Methods of Polypeptide Delivery

In some embodiments, the chimeric CD154 polypeptide is delivered in nanoparticles. For example, the nanoparticles are made of biodegradable polymers such as poly lactic acid, polycaprolactone, poly(lactic-co-glycolic acid), the poly(fumaric-co-sebacic) anhydride chitosan, and modified chitosan. Alternatively, the chimeric CD154 polypeptide is delivered in liposomes, PEGylated liposomes, niosomes, or aquasomes. Other methods known in the art for peptide or protein delivery may be used such as described in U.S. Pat. Nos. 8,288,113 and 5,641,670, and U.S. Patent Publication Nos. US20100291065, US20140242107, US2014023213, US20150191710 and US2010026678; all of which are incorporated herein by reference.

In some embodiments, the chimeric CD154 polypeptide is provided in an expression construct. In particular, the chimeric CD154 construct would be membrane-stabilized and resistant to proteolytic cleavage, and thereby less likely to generate the soluble form of CD154. However, the chimeric CD154 construct would maintain the receptor-binding function of native CD154. Moreover, a particular CD154 construct would not be immunogenic at the domain critical for receptor binding following administration in humans, thus avoiding functional neutralization.

One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc.), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors.

1. Viral Vectors

Viral vectors encoding the chimeric CD154 polypeptide may be provided in certain aspects of the present invention. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

a. Adenoviral Vector

One method for delivery of the chimeric CD154 polypeptide involves the use of an adenovirus expression vector. Although adenovirus vectors are known to have a low capacity for integration into genomic DNA, this feature is counterbalanced by the high efficiency of gene transfer afforded by these vectors. Adenovirus expression vectors include constructs containing adenovirus sequences sufficient to (a) support packaging of the construct and (b) to ultimately express a recombinant gene construct that has been cloned therein.

Adenovirus growth and manipulation is known to those of skill in the art, and exhibits broad host range in vitro and in vivo. This group of viruses can be obtained in high titers, e.g., 109-1011 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them particular mRNA's for translation.

A recombinant adenovirus provided herein can be generated from homologous recombination between a shuttle vector and provirus vector. Due to the possible recombination between two proviral vectors, wild-type adenovirus may be generated from this process. Therefore, a single clone of virus is isolated from an individual plaque and its genomic structure is examined.

The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the particular starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Nucleic acids can be introduced to adenoviral vectors as a position from which a coding sequence has been removed. For example, a replication defective adenoviral vector can have the E1-coding sequences removed. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Generation and propagation of replication deficient adenovirus vectors can be performed with helper cell lines. One unique helper cell line, designated 293, was transformed from human embryonic kidney cells by Ad5 DNA fragments and constitutively expresses E1 proteins (Graham et al., 1977). Since the E3 region is dispensable from the adenovirus genome (Jones and Shenk, 1978), adenovirus vectors, with the help of 293 cells, carry foreign DNA in either the E1, the E3, or both regions (Graham and Prevec, 1991).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a particular helper cell line is 293.

Methods for producing recombinant adenovirus are known in the art, such as U.S. Pat. No. 6,740,320, incorporated herein by reference. Also, Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/1) are employed as follows. A cell inoculum, resuspended in 5 ml of medium, is added to the carrier (50 ml) in a 250 ml Erlenmeyer flask and left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

b. Retroviral Vector

Additionally, the chimeric CD145 polypeptide may be encoded by a retroviral vector. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, packaging cell lines are available that should greatly decrease the likelihood of recombination (Markowitz et al., 1988; Hersdorffer et al., 1990).

c. Adeno-Associated Viral Vector

Adeno-associated virus (AAV) is an attractive vector system for use in the present disclosure as it has a high frequency of integration and it can infect nondividing cells, thus making it useful for delivery of genes into mammalian cells (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. Nos. 5,139,941 and 4,797,368.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

d. Other Viral Vectors

Other viral vectors may be employed as constructs in the present disclosure. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997).

In further embodiments, the nucleic acid encoding chimeric CD154 is housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

For example, targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements.

The cellular machinery is able to gather and integrate the regulatory information conveyed by each element, allowing different genes to evolve distinct, often complex patterns of transcriptional regulation. A promoter used in the context of the present invention includes constitutive, inducible, and tissue-specific promoters.

a. Promoter/Enhancers

The expression constructs provided herein comprise a promoter to drive expression of the programming genes. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007).

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

b. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Additionally, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the F2A (Foot-and-mouth disease virus 2A) or a "2A-like" sequence (e.g., *Thosea asigna* virus 2A; T2A) (Minskaia and Ryan, 2013).

c. Of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

3. Selection and Screenable Markers

In some embodiments, cells containing a construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

C. Nucleic Acid Delivery

In addition to viral delivery of the nucleic acids encoding chimeric CD154, the following are additional methods of recombinant gene delivery to a given host cell and are thus considered in the present disclosure.

Introduction of a nucleic acid, such as DNA or RNA, may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Electroporation

In certain particular embodiments of the present disclosure, the gene construct is introduced into target hyperproliferative cells via electroporation. Electroporation involves the exposure of cells (or tissues) and DNA (or a DNA complex) to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

It is contemplated that electroporation conditions for hyperproliferative cells from different sources may be optimized. One may particularly wish to optimize such parameters as the voltage, the capacitance, the time and the electroporation media composition. The execution of other routine adjustments will be known to those of skill in the art. See e.g., Hoffman, 1999; Heller et al., 1996.

2. Lipid-Mediated Transformation

In a further embodiment, the chimeric CD154 may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Feigner et al., 1987) and in vivo gene transfer (Zhu el al., 1993; Philip et al., 1993; Solodin et al., 1995; Liu et al., 1995; Thierry et al., 1995; Tsukamoto et al., 1995; Aksentijevich et al., 1996).

Advances in lipid formulations have improved the efficiency of gene transfer in vivo (Templeton et al. 1997; WO 98/07408). A novel lipid formulation composed of an equimolar ratio of 1,2-bis(oleoyloxy)-3-(trimethyl ammonio) propane (DOTAP) and cholesterol significantly enhances systemic in vivo gene transfer, approximately 150 fold. The DOTAP:cholesterol lipid formulation forms unique structure termed a “sandwich liposome”. This formulation is reported to “sandwich” DNA between an invaginated bilayer or ‘vase’ structure. Beneficial characteristics of these lipid structures include a positive ρ, colloidal stabilization by cholesterol, two dimensional DNA packing and increased serum stability. Patent Application Nos. 60/135,818 and 60/133,116 discuss formulations that may be used with the present invention.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

III. TLR Agonists

The present disclosure provides methods of combining a TLR agonist with CD40 activation, such as chimeric CD154 polypeptide.

The TLR agonists may be drugs such as small molecules, recombinant forms of ligand or receptors, antibodies, such as human antibodies. Known TLR agonists or analogs thereof may be used, in particular small molecules. As the skilled person will know, alternative and/or equivalent names may be in use for certain TLR agonists mentioned in the present disclosure. Such alternative and/or equivalent names are interchangeable in the context of the present invention.

IV. Methods of Treatment

Provided herein are methods for treating or delaying progression of cancer in an individual comprising administering to the individual an effective amount of at least one TLR agonist and a CD40 agonist (e.g., chimeric CD154 polypeptide). Any of the TLR agonists and the CD40 agonists (e.g., chimeric CD154 polypeptide) known in the art or described herein may be used in the methods provided herein.

In some embodiments, the treatment results in a sustained response in the individual after cessation of the treatment. The methods described herein may find use in treating conditions where enhanced immunogenicity is desired such as increasing tumor immunogenicity for the treatment of cancer. Also provided herein are methods of enhancing immune function such as in an individual having cancer comprising administering to the individual an effective amount of TLR agonist and a chimeric CD154 polypeptide. In some embodiments, the individual is a human.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

The efficacy of any of the methods described herein (e.g., combination treatments including administering an effective amount of a combination of at least one TLR agonist and a chimeric CD154 polypeptide may be tested in various models known in the art, such as clinical or pre-clinical models. Suitable pre-clinical models are exemplified herein and further may include without limitation ID8 ovarian cancer, GEM models, B16 melanoma, RENCA renal cell cancer, CT26 colorectal cancer, MC38 colorectal cancer, LLC lung cancer, MBT-2 bladder cancer, and Cloudman melanoma models of cancer.

In some embodiments of the methods of the present disclosure, the cancer has low levels of T cell infiltration. In some embodiments, the cancer has no detectable T cell infiltrate. In some embodiments, the cancer is a non-immunogenic cancer (e.g., non-immunogenic colorectal cancer and/or ovarian cancer). Without being bound by theory, the combination treatment may increase T cell (e.g., $CD4^+$ T cell, $CD8^+$ T cell, memory T cell) priming, activation and/or proliferation relative to prior to the administration of the combination.

In some embodiments of the methods of the present disclosure, activated CD4 and/or CD8 T cells in the individual are characterized by γ-IFN producing CD4 and/or CD8 T cells and/or enhanced cytolytic activity relative to prior to the administration of the combination. γ-IFN may be measured by any means known in the art, including, e.g., intracellular cytokine staining (ICS) involving cell fixation, permeabilization, and staining with an antibody against γ-IFN. Cytolytic activity may be measured by any means known in the art, e.g., using a cell killing assay with mixed effector and target cells.

The present disclosure is useful for any human cell that participates in an immune reaction either as a target for the immune system or as part of the immune system's response to the foreign target. The methods include ex vivo methods, in vivo methods, and various other methods that involve injection of polynucleotides or vectors into the host cell. The methods also include injection directly into the tumor or tumor bed as well as local or regional to the tumor.

The present invention thus contemplates ex vivo methods comprising isolation of cells from an animal or human subject. A polynucleotide sequence encoding a chimeric CD154 is introduced into the isolated cells. The cells are then re-introduced at a specific site or directly into the circulation of the subject. Cell surface markers, including molecules such as tumor markers or antigens that identify the cells, may be used to specifically isolate these cells from the subject.

A. Administration

The combination therapy provided herein comprises administration of a TLR agonist and a chimeric CD154 polypeptide. The combination therapy may be administered in any suitable manner known in the art. For example, a TLR agonist and a chimeric CD154 polypeptide may be administered sequentially (at different times) or concurrently (at the same time). In some embodiments, the TLR agonist is in a separate composition as the chimeric CD154 polypeptide or expression construct thereof. In some embodiments, the TLR agonist is in the same composition as the chimeric CD154 polypeptide.

The TLR agonist and the chimeric CD154 polypeptide may be administered by the same route of administration or by different routes of administration. In some embodiments, the TLR agonist is administered intravenously, intramuscularly, subcutaneously, topically, orally, transdermally, intraperitoneally, intraorbitally, by implantation, by inhalation, intrathecally, intraventricularly, intratumorally, intronodally, or intranasally. In some embodiments, the chimeric CD40 polypeptide is administered intravenously, intramuscularly, subcutaneously, topically, orally, transdermally, intraperitoneally, intraorbitally, by implantation, by inhalation, intrathecally, intraventricularly, intratumorally, intronodally, or intranasally. An effective amount of the TLR agonist and the chimeric CD154 polypeptide may be administered for prevention or treatment of disease. The appropriate dosage of TLR agonist and/or the chimeric CD154 polypeptide may be determined based on the type of disease to be treated, severity and course of the disease, the clinical condition of the individual, the individual's clinical history and response to the treatment, and the discretion of the attending physician. In some embodiments, combination treatment with at least one TLR agonist and a CD154 polypeptide are synergistic, whereby an efficacious dose of a chimeric CD154 polypeptide in the combination is reduced relative to efficacious dose of at the TLR agonist as a single agent.

For example, in certain embodiments the therapeutically effective amount of the TLR agonist, such as a small molecule, and/or the chimeric CD154 polypeptide or expression construct thereof that is administered to a human will be in the range of about 0.01 to about 50 mg/kg of patient body weight whether by one or more administrations. The progress of this therapy is easily monitored by conventional techniques and concentrations may be altered as needed.

Intratumoral injection, or injection into the tumor vasculature is specifically contemplated for discrete, solid, accessible tumors. Local, regional or systemic administration also may be appropriate.

Treatment regimens may vary as well, and often depend on tumor type, tumor location, disease progression, and health and age of the patient. Obviously, certain types of tumors will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic viral constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

B. Pharmaceutical Formulations

Also provided herein are pharmaceutical compositions and formulations comprising at least one TLR agonist and a chimeric CD154 polypeptide (e.g. ad-ISF35), and a pharmaceutically acceptable carrier.

Pharmaceutical compositions and formulations as described herein can be prepared by mixing the active ingredients (such as a small molecule or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The composition and formulation herein may also contain more than one active ingredients as necessary for the particular indication being treated, in particular those with complementary activities that do not adversely affect each other. Such active ingredients are suitably present in combination in amounts that are effective for the purpose intended.

C. Additional Therapies

In some embodiments, the methods may further comprise an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

The additional therapy may be an antagonist directed against B7-H3 (also known as CD276), e.g., a blocking antibody, MGA271, an antagonist directed against a TGF beta, e.g., metelimumab (also known as CAT-192), fresolimumab (also known as GC1008), or LY2157299, a treatment comprising adoptive transfer of a T cell (e.g., a cytotoxic T cell or CTL) expressing a chimeric antigen receptor (CAR), a treatment comprising adoptive transfer of a T cell comprising a dominant-negative TGF beta receptor, e.g, a dominant-negative TGF beta type II receptor, a treatment comprising a HERCREEM protocol (see, e.g., ClinicalTrials.gov Identifier NCT00889954), an agonist directed against CD137 (also known as TNFRSF9, 4-1BB, or ILA), e.g., an activating antibody, urelumab (also known as BMS-663513), an agonist directed against OX40 (also known as CD134), e.g., an activating antibody, administered in conjunction with a different anti-OX40 antibody (e.g., AgonOX), an agonist directed against CD27, e.g., an activating antibody, CDX-1127, indoleamine 2,3-dioxygenase (IDO), 1-methyl-D-tryptophan (also known as 1-D-MT), an antibody-drug conjugate (in some embodiments, comprising mertansine or monomethyl auristatin E (MMAE)), an anti-NaPi2b antibody-MMAE conjugate (also known as DNIB0600A or RG7599), trastuzumab emtansine (also known as T-DM1, ado-trastuzumab emtansine, or KADCYLA®, Genentech), DMUC5754A, an antibody-drug conjugate targeting the endothelin B receptor (EDNBR), e.g., an antibody directed against EDNBR conjugated with MMAE, an angiogenesis inhibitor, an antibody directed against a VEGF, e.g., VEGF-A, bevacizumab (also known as AVASTIN®, Genentech), an antibody directed against angiopoietin 2 (also known as Ang2), MEDI3617, an antineoplastic agent, an agent targeting CSF-1R (also known as M-CSFR or CD 115), anti-CSF-1R (also known as IMC-CS4), an interferon, for example interferon alpha or interferon gamma, Roferon-A, GM-CSF (also known as recombinant human granulocyte macrophage colony stimulating factor, rhu GM-CSF, sargramostim, or Leukine®), IL-2 (also known as aldesleukin or Proleukin®), IL-12, an antibody targeting CD20 (in some embodiments, the antibody targeting CD20 is obinutuzumab (also known as GA101 or Gazyva®) or rituximab), an antibody targeting GITR (in some embodiments, the antibody targeting GITR is TRX518), in conjunction with a cancer vaccine (in some embodiments, the cancer vaccine is a peptide cancer vaccine, which in some embodiments is a personalized peptide vaccine; in some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104: 14-21, 2013)), in conjunction with an adjuvant, a TLR agonist, e.g., Poly-ICLC (also known as Hiltonol®), LPS, MPL, or CpG ODN, tumor necrosis factor (TNF) alpha, IL-1, HMGB1, an IL-10 antagonist, an IL-4 antagonist, an IL-13 antagonist, an HVEM antagonist, an ICOS agonist, e.g., by administration of ICOS-L, or an agonistic antibody directed against ICOS, a treatment targeting CX3CL1, a treatment targeting CXCL10, a treatment targeting CCLS, an LFA-1 or ICAM1 agonist, a Selectin agonist, a targeted therapy, an inhibitor of B-Raf, vemurafenib (also known as Zelboraf®, dabrafenib (also known as Tafinlar®), erlotinib (also known as Tarceva®), an inhibitor of a MEK, such as MEK1 (also known as MAP2K1) or MEK2 (also known as MAP2K2) cobimetinib (also known as GDC-0973 or XL-518), trametinib (also known as Mekinist®), an inhibitor of K-Ras, an inhibitor of c-Met, onartuzumab (also known as MetMAb), an inhibitor of Alk, AF802 (also known as CH5424802 or alectinib), an inhibitor of a phosphatidylinositol 3-kinase (PI3K), BKM120, idelalisib (also known as GS-1101 or CAL-101), perifosine (also known as KRX-0401), an Akt, MK2206, GSK690693, GDC-0941, an inhibitor of mTOR, sirolimus (also known as rapamycin), temsirolimus (also known as CCI-779 or Torisel®), everolimus (also known as RAD001), ridaforolimus (also known as AP-23573, MK-8669, or deforolimus), OSI-027, AZD8055, INK128, a dual PI3K/mTOR inhibitor, XL765, GDC-0980, BEZ235 (also known as NVP-BEZ235), BGT226, GSK2126458, PF-04691502, PF-05212384 (also known as PKI-587).

V. Articles of Manufacture or Kits

An article of manufacture or a kit is provided comprising a TLR agonist and a chimeric CD154 polypeptide (e.g. ad-ISF35) is also provided herein. The article of manufacture or kit can further comprise a package insert comprising instructions for using the TLR agonist in conjunction with a chimeric CD154 polypeptide to treat or delay progression of cancer in an individual or to enhance immune function of an individual having cancer. Any of the TLR agonists and/or chimeric CD154 polypeptides described herein may be included in the article of manufacture or kits. In some embodiments, a TLR agonist and a chimeric CD154 polypeptide (e.g., ad-ISF35) are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

All of the methods disclosed and claimed herein can be made and executed without undue experimentation in light of the present disclosure. While the compositions and methods of this invention have been described in terms of particular embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of enhancing function of an immune cell in a subject comprising: administering to the subject a combination of a chimeric CD154 polypeptide and at least one Toll Like Receptor (TLR) agonist, wherein said chimeric CD154 polypeptide comprises (a) an extracellular subdomain of human CD154 that binds to a human CD154 receptor and (b) an extracellular subdomain of non-human CD154 that has replaced a cleavage site of human CD154; and wherein said subject is not administered an antibody, antibody fragment, or antigen binding molecule targeting GITR.

2. The method of claim 1, wherein the at least one TLR agonist is selected from the group consisting of TLR1, TLR2, TLR3, TLR4, TLR5, TLR6, TLR7, TLR8, TLR9, TLR10, TLR11, and TLR7/8 agonists.

3. The method of claim 1, wherein the extracellular subdomain of non-human CD154 is an extracellular subdomain of murine CD154.

4. The method of claim 1, wherein the chimeric CD154 polypeptide is selected from the group consisting of ISF30, ISF31, ISF32, ISF33, ISF34, ISF35, ISF36, ISF37, ISF38, ISF39, ISF40, and ISF41.

5. The method of claim 1, wherein the chimeric CD154 polypeptide is ISF35.

6. The method of claim 1, wherein the chimeric CD154 polypeptide is administered to a subject by providing a coding region for the chimeric CD154 polypeptide in an expression vector under control of a promoter active in a eukaryotic cell.

7. The method of claim 6, wherein the expression vector is a viral vector.

8. The method of claim 7, wherein the viral vector is an adenoviral vector, a retroviral vector, a pox viral vector, a herpesviral vector, an adeno-associated viral vector, or a polyoma viral vector.

9. The method of claim 8, wherein the viral vector is an adenoviral vector.

10. A method of treating cancer in a subject comprising:

(a) removing one or more immune cells from the subject;

(b) culturing said immune cells with one or more eukaryotic cells containing a coding region for a chimeric CD154 polypeptide in an expression vector under control of a promoter active in the eukaryotic cells under conditions supporting expression of the CD154 polypeptide;

(c) administering at least a portion of said cultured immune cells back into the subject; and (d) administering an effective amount of at least one Toll Like Receptor (TLR) agonist, wherein said subject is not administered an antibody, antibody fragment, or antigen binding molecule targeting GITR.

* * * * *